(12) United States Patent
Miao et al.

(10) Patent No.: US 10,492,751 B2
(45) Date of Patent: Dec. 3, 2019

(54) METHOD AND APPARATUS FOR MODULATING X-RAY TUBE CURRENT IN COMPUTED TOMOGRAPHY

(71) Applicant: FMI Medical Systems Co., Ltd., Zhejiang (CN)

(72) Inventors: Chuang Miao, Macedonia, OH (US); Abdelaziz Ikhlef, Hudson, OH (US)

(73) Assignee: FMI Medical Systems Co., Ltd., Zhejiang (CN)

( * ) Notice: Subject to any disclaimer, the term of this patent is extended or adjusted under 35 U.S.C. 154(b) by 102 days.

(21) Appl. No.: 15/895,391

(22) Filed: Feb. 13, 2018

(65) Prior Publication Data
US 2019/0247001 A1    Aug. 15, 2019

(51) Int. Cl.
*A61B 6/00* (2006.01)
*A61B 6/03* (2006.01)

(52) U.S. Cl.
CPC ............ *A61B 6/544* (2013.01); *A61B 6/035* (2013.01); *A61B 6/40* (2013.01); *A61B 6/4233* (2013.01); *A61B 6/488* (2013.01); *A61B 6/545* (2013.01); *A61B 6/583* (2013.01)

(58) Field of Classification Search
CPC ......... A61B 6/035; A61B 6/40; A61B 6/4233; A61B 6/488; A61B 6/544; A61B 6/545; A61B 6/583
See application file for complete search history.

(56) References Cited

U.S. PATENT DOCUMENTS

| | | | |
|---|---|---|---|
| 5,379,333 A | 1/1995 | Toth | |
| 5,400,378 A | 3/1995 | Toth | |
| 5,450,462 A | 9/1995 | Toth et al. | |
| 5,696,807 A | 12/1997 | Hsieh | |
| 10,085,698 B2 * | 10/2018 | Fan | A61B 6/032 |
| 2004/0264628 A1 * | 12/2004 | Besson | A61B 6/032 378/5 |
| 2007/0258559 A1 * | 11/2007 | Hur | A61B 6/481 378/16 |
| 2014/0270053 A1 * | 9/2014 | Larson | A61B 6/032 378/4 |
| 2014/0376688 A1 * | 12/2014 | Karmazyn | A61B 6/032 378/8 |
| 2017/0143291 A1 * | 5/2017 | Guntzer | A61B 6/032 |

OTHER PUBLICATIONS

Techniques and Applications of Automatic Tube Current Modulation for CT1; Radiology; Dec. 2004 by Mannudeep K. Kaira, MD, DNB et al.

* cited by examiner

*Primary Examiner* — Marcus H Taningco
(74) *Attorney, Agent, or Firm* — Fishman Stewart PLLC

(57) ABSTRACT

A computed tomography (CT) system includes a rotatable gantry having an opening to receive an object to be scanned, a high-voltage generator, an x-ray tube positioned on the gantry to generate x-rays through the opening, a pixelated detector positioned on the gantry to receive the x-rays, and a computer. The computer is programmed to obtain a scout image of the object, calculate an equivalent diameter of a water cylinder based on the scout image over a length of the scout image, calculate a major axis and a minor axis for an equivalent ellipse over the length, calculate, based on a noise index and based on the equivalent diameter as the function of the length, an mA modulation as a function of the length, and obtain image data of the object by modulating an mA applied to the x-ray tube based on the calculated mA modulation.

20 Claims, 12 Drawing Sheets

METHOD AND APPARATUS FOR MODULATING X-RAY TUBE CURRENT IN COMPUTED TOMOGRAPHY

TECHNICAL FIELD

This disclosure relates generally to diagnostic imaging and, more particularly, to a method and apparatus for reducing dose in a computed tomography (CT) system.

BACKGROUND

Typically, in computed tomography (CT) imaging systems, a rotatable gantry includes an x-ray tube, detector, data acquisition system (DAS), and other components that rotate about a patient that is positioned at the approximate rotational center of the gantry. X-rays emit from the x-ray tube, are attenuated by the patient, and are received at the detector. The detector typically includes a photodiode-scintillator array of pixelated elements that convert the attenuated x-rays into photons within the scintillator, and then to electrical signals within the photodiode. The electrical signals are digitized and then received within the DAS, processed, and the processed signals are transmitted via a slipring (from the rotational side to the stationary side) to a computer or data processor for image reconstruction, where an image is formed.

The gantry typically includes a pre-patient collimator that defines or shapes the x-ray beam emitted from the x-ray tube. X-rays passing through the patient can cause x-ray scatter to occur, which can cause image artifacts. Thus, x-ray detectors typically include an anti-scatter grid (ASG) for collimating x-rays received at the detector. Imaging data may be obtained using x-rays that are generated at a single polychromatic energy. However, some systems may obtain multi-energy images that provide additional information for generating images.

Third generation multi-slices CT scanners typically include a detector assembly having scintillator/photodiodes arrays positioned in an arc, where the focal spot is the center of the corresponding circle. The material used in these detectors generally has scintillation crystal/photodiode arrays, where the scintillation crystal absorbs x-rays and converts the absorbed energy into visible light. A photodiode is used to convert the light to an electric current. The reading is typically proportional and linear to the total energy absorbed in the scintillator.

A helical scan may be performed, in which the patient is moved while data is acquired for a number of slices. A helix mapped out by a fan beam yields projection data from which images in each slice may be reconstructed. Scanning parameters, such as x-ray tube or filament current "mA", x-ray tube supply voltage "kV", slice thickness, scan time, and helical pitch, can affect image quality. In addition, the x-ray tube current relates to patient x-ray dose. Typically, higher tube current improves image quality, but likewise increases patient dose. To reduce dose, x-ray tube current may be reduced, but insufficient x-ray tube current levels can result in steaking artifacts in the image.

Traditionally, to ensure sufficient image quality, an operator typically prescribes a high dose and at a fixed current level to provide a constant dose during the entire scan. However, such a dose often includes excessive x-ray flux during portions of the scan when patient attenuation is low (and thus the excess flux is unnecessary). On the other hand, if the fixed level is too low, then noise artifacts may appear in the image where the beam is highly attenuated.

Scanning algorithms have been developed as an attempt to reduce patient dose and address the aforementioned issues. For instance, one known method modulates x-ray tube current as a function of slice location. However, such an arrangement can still result in excess x-ray dose at rotational gantry angles where there is small attenuation. Another known algorithm includes modulating x-ray tube current as a function of gantry angle. However, this system may include excessive dose because attenuation characteristics of, for instance, a lung region are much smaller than a shoulder region. One known system modulates x-ray tube current as a function of both gantry angle and slice location, but in such system a modulating factor is updated during a scan and based on real photon readings.

Further, such known systems may include two scout scans such that sufficient information related to a scan may be obtained prior to actual imaging—resulting in excess dose due to the two scout scans.

Thus, there is a need to reduce patient dose while maintaining sufficient x-ray tube current to avoid streaking artifacts.

BRIEF DESCRIPTION

The disclosure is directed toward an apparatus, method of fabricating, in computed tomography (CT)

A computed tomography (CT) system includes a rotatable gantry having an opening to receive an object to be scanned, a high-voltage generator, an x-ray tube positioned on the gantry to generate x-rays through the opening, a pixelated detector positioned on the gantry to receive the x-rays, and a computer. The computer is programmed to obtain a scout image of the object, calculate an equivalent diameter of a water cylinder based on the scout image over a length of the scout image, calculate a major axis and a minor axis for an equivalent ellipse over the length, calculate, based on a noise index and based on the equivalent diameter as the function of the length, an mA modulation as a function of the length, and obtain image data by modulating an mA applied to the x-ray tube based on the calculated mA modulation.

A method of obtaining image data for a computed tomography (CT) system includes obtaining a scout image of an object, calculating an equivalent diameter of a water cylinder based on the scout image over a length of the scout image, calculating a major axis and a minor axis for an equivalent ellipse over the length, calculating, based on a noise index and based on the equivalent diameter as the function of the length, an mA modulation as a function of the length, and obtaining image data by modulating an mA applied to the x-ray tube based on the calculated mA modulation.

A computer readable storage medium having stored thereon a computer comprising instructions, which, when executed by a computer, cause the computer to obtain a scout image of the object, calculate an equivalent diameter of a water cylinder based on the scout image over a length of the scout image, calculate a major axis and a minor axis for an equivalent ellipse over the length, calculate, based on a noise index and based on the equivalent diameter as the function of the length, an mA modulation as a function of the length, and obtain image data by modulating an mA applied to the x-ray tube based on the calculated mA modulation.

Various other features and advantages will be made apparent from the following detailed description and the drawings.

DETAILED DESCRIPTION

The operating environment of disclosed examples is described with respect to a multislice computed tomography (CT) system. Examples are described with respect to a "third generation" CT scanner, however it is contemplated that the disclosed examples are applicable to other imaging systems as well, and for CT systems having more or less than the illustrated sixty-four-slice system.

The present disclosure includes a method to substitute current reference channels used for projection data normalization by a factor based on a feedback current (mA) generated from a high voltage generator.

Figure 1:
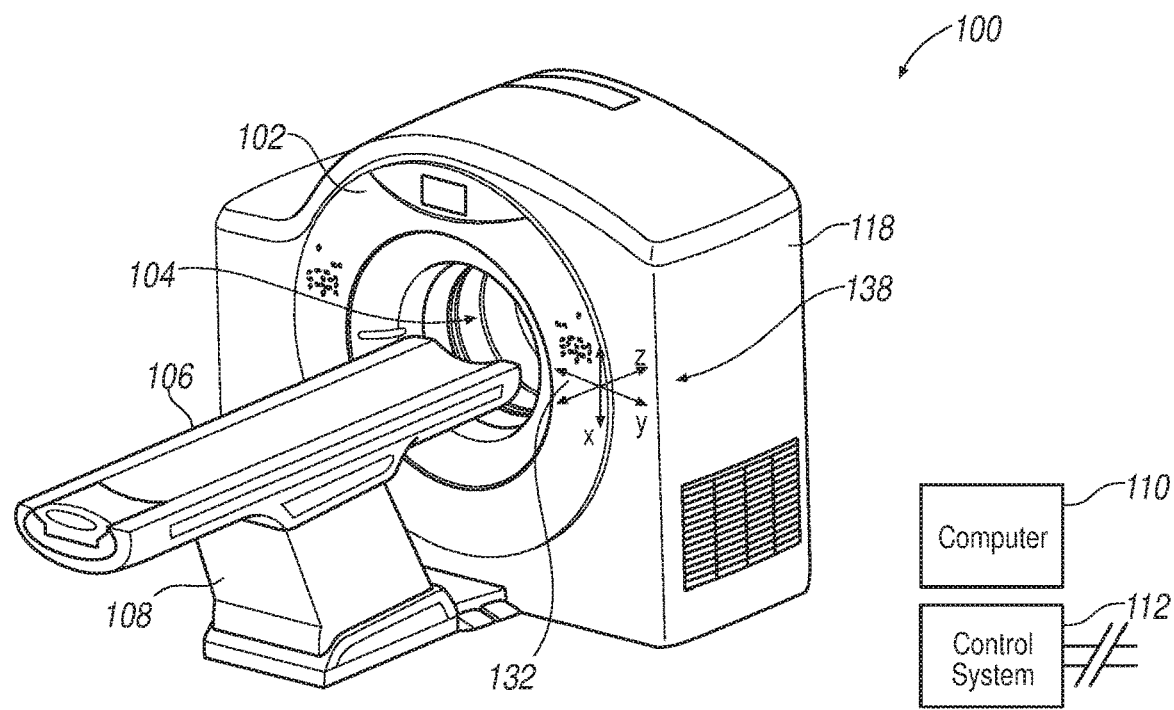
FIG. 1 is a perspective view of a CT imaging system.
Figure 2:
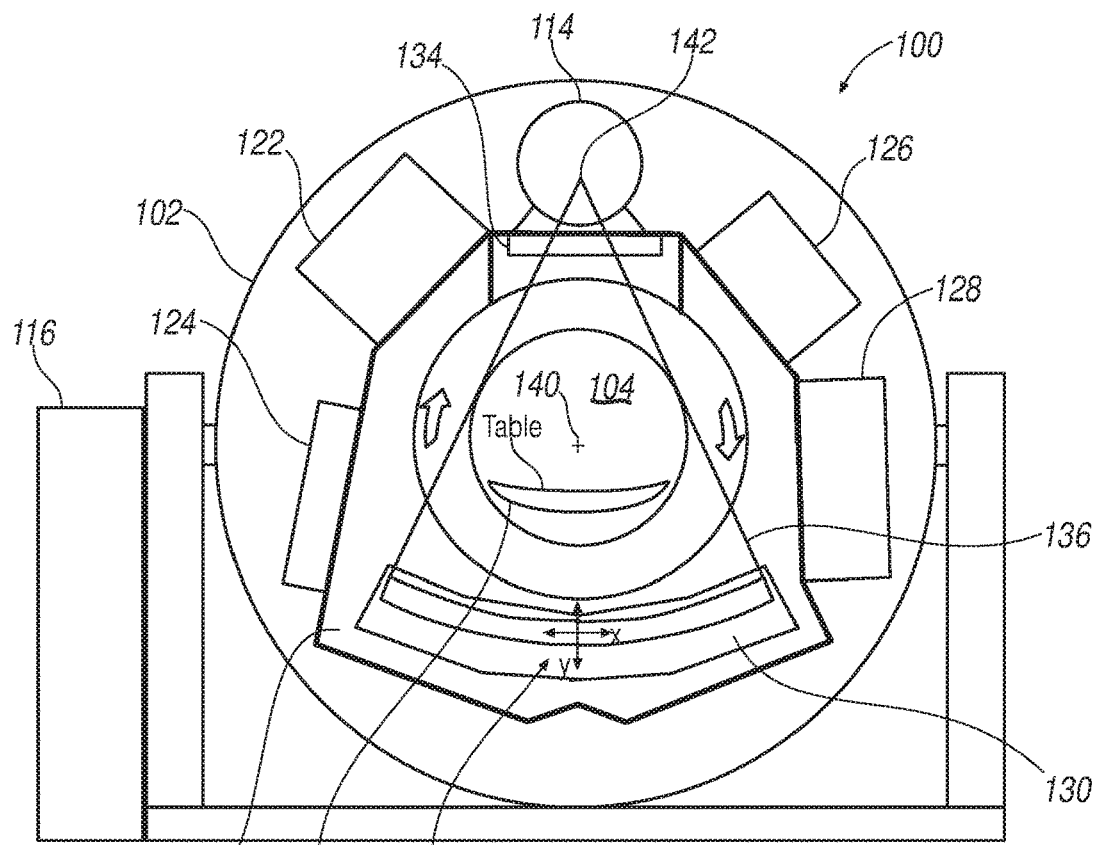
FIG. 2 is a planar cross-section of the system illustrated in FIG. 1.

Referring to FIGS. 1 and 2, a computed tomography (CT) system 100 includes a gantry 102 having an opening 104. A patient table 106 is positioned on a support structure 108, and patient table 106 is axially controllable such that a patient (not shown) positioned on table 106 may be positioned within opening 104. A computer system 110 provides operator instructions and other control instructions to a control system 112. Computer system 110 also may include image reconstruction programs, or an image reconstructor may be provided as a separate processing unit. Control system 112 provides control commands for operating gantry 102, an x-ray tube 114, and a gantry motor controller 116, as examples. Gantry 102 includes a cover or enclosure 118, which provides for aesthetic improvement, safety, etc.

Gantry 102 includes a rotatable base 120, on which is mounted x-ray tube 114, a heat exchanger 122, a data acquisition system (DAS) 124, an inverter 126, a high-voltage generator 128 for generating high voltage in x-ray tube 114, and a detector assembly 130, as examples. System 100 is operated with commands entered by a user into computer 110. Gantry 102 may include gantry controls 132 located thereon, for convenient user operation of some of the commands for system 100. Detector assembly 130 includes a plurality of detector modules (not shown), which include an anti-scatter grid (ASG), scintillators, photodiodes, and the like, which detect x-rays and convert the x-rays to electrical signals, from which imaging data is generated. Gantry 102 includes a pre-patient collimator 134 that is positioned to define or shape an x-ray beam 136 emitted from x-ray tube 114. Although not shown, a shape filter may be positioned for instance between x-ray tube 114 and pre-patient collimator 134.

In operation, rotatable base 120 is rotating about the patient, and table 106 is enabled to move the patient axially into the opening 104. When a desired imaging location of the patient is proximate an axial location where x-ray beam 136 will be caused to emit, x-ray tube 114 is energized and x-ray beam 136 is generated from a focal spot within x-ray tube 114. The detectors receive x-rays, some of which have passed through the patient, yielding analog electrical signals that are digitized and passed to DAS 124, and then to computer 110 where the data is further processed to generate an image. The imaging data are stored on computer system 100 and images may be viewed. An X-Y-Z triad 138, corresponding to a local reference frame for components that rotate on rotatable base 120, defines a local directional coordinate system in a gantry circumferential direction X, a gantry radial direction Y, and gantry axial direction Z. Accordingly, and referring to triad 138, the patient passes parallel to the Z-axis, the x-rays pass along the Y axis, and the rotational components (such as detector assembly 130) rotate in a circumferential direction and in the X direction, and about an isocenter 140 (which is a centerpoint about which rotatable base rotates, and is an approximate position of the patient for imaging purposes). A focal spot 142 is illustrated within x-ray tube 114, which corresponds to a spot from which x-ray beam 136 emits.

Figure 3:
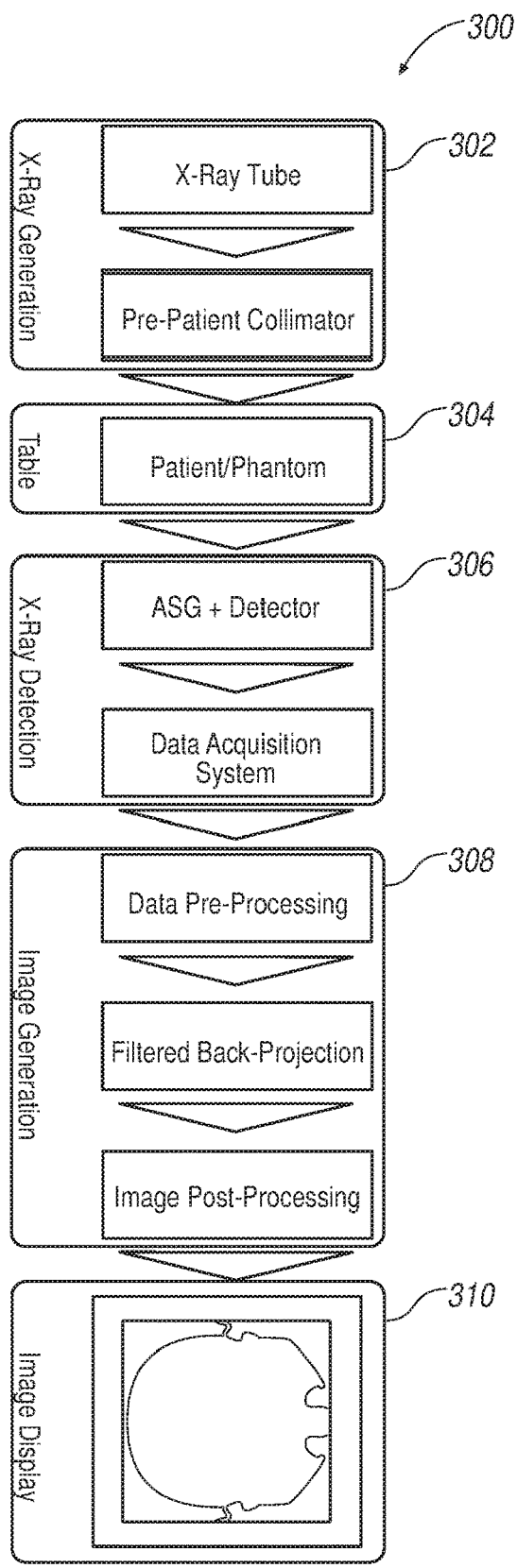
FIG. 3 is an example of an imaging chain.

FIG. 3 illustrates an exemplary image chain 300, consistent with the operation described with respect to FIGS. 1 and 2. X-ray generation 302 occurs, using x-ray tube 114 and passing x-rays through pre-patient collimator 134, during which patient table 106 passes 304 through opening 104 of gantry 102. In one example table 106 may have a patient thereon, and in another example a phantom may be used for calibration purposes.

X-ray detection 306 occurs when x-rays having been emitted from x-ray tube 114 pass to detector assembly 130. An anti-scatter grid (ASG) prevents x-ray scatter (emitting for example from the patient as secondary x-rays and in a direction that is oblique to x-ray beam 136), by generally filtering x-rays that emit from x-ray tube 114. DAS 124 processes signals received from detector assembly 130. Image generation 308 occurs after the digitized signals are passed from a rotating side of gantry 102 (on rotatable base 120) to a stationary side, via for instance a slip-ring.

Image generation 308 occurs in computer system 110, or in a separate processing module that is in communication with computer system 110. The data is pre-processed, and image views or projections are used to reconstruct images using known techniques such as a filtered backprojection (FBP). Image post-processing also occurs, after which the images may be displayed 310, or otherwise made available for display elsewhere (such as in a remote computing device).

Figure 4:
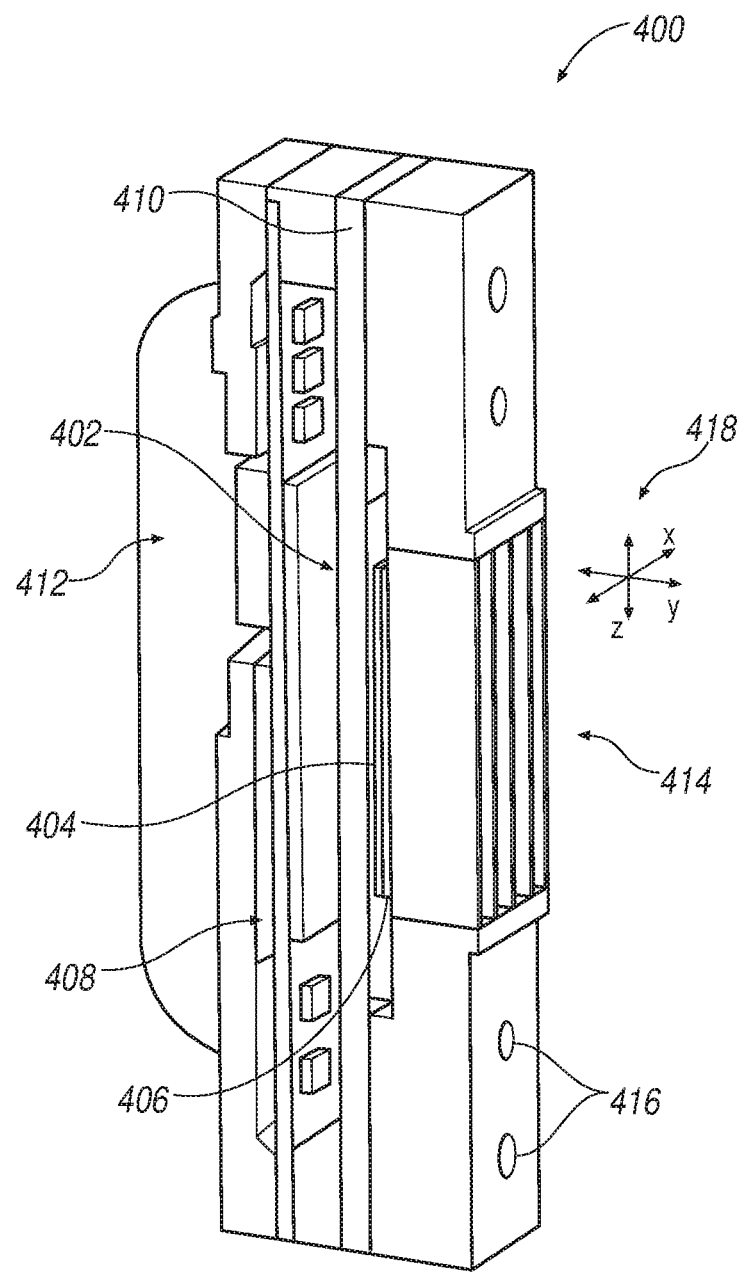
FIG. 4 is an example of a detector module.

FIG. 4 illustrates an exemplary detector module 400 that is one of a plurality of modules for use in detector assembly 130. A diode-scintillator array 402 includes a pixelated scintillator 406 positioned on a pixelated photodiode array 404. The photodiode array 404 may be either a front-lit or a back-lit type of photodiode. The diode-scintillator array 402 is positioned on an A/D board 408 that includes electronics components for signal processing, wherein analog electrical signals from diode-scintillator array 402 are digitized and then passed to DAS 124. Diode-scintillator array 402 is positioned on a base substrate 410 that may include a ceramic or other solid base material. A heat sink 412 is in thermal contact with A/D board 408 for providing enhanced cooling to the electronics located on A/D board 408. Detector module 400 also includes an anti-scatter grid (ASG) 414 that, in one example, includes a plurality of plates (a few exemplary plates are shown) that are approximately parallel with a Y-Z plane of detector assembly 130. ASG 414, in the illustrated example, includes mount holes 416 which may be used for mounting module 400 to detector assembly 130 and aligning it therewith. FIG. 4 illustrates a triad 418 that illustrates corresponding X-Y-Z coordinates, as illustrated also in FIG. 1.

The present disclosure, in one form, includes an x-ray CT system for modulating x-ray tube current as a function of gantry angle and slice location to reduce the patient dose without significantly degrading image quality, including at least the following improvements. A method is disclosed to calculate the water equivalent cylinder area, and then calculate a water equivalent elliptical size. A filtering operation is performed after the calculation of a water equivalent phantom size, which makes the modulated tube current profile smooth and makes the system stable. A power function based noise—mA relationship is disclosed, and an interpolation strategy is disclosed to calculate noise for any water phantom size at a given tube current. The disclosed interpolation strategy can be applied to calculate a modulated mA values for any phantom size to achieve certain and desired noise level.

A modulating factor is derived mathematically as a function of slice location based on the calculated water equivalent phantom size from only one scout image. According to the disclosure, only one scout image is needed, avoiding the additional time and dose typically used to obtain two scout images. Eight x-ray tube current sectors around one rotation are selected. Each sector covers angle range 45 degrees. Specifically, according to the disclosure the first sector starts at −22.5 degrees instead of 0 degree. Noise level is automatically determined and not prescribed by a user. An average x-ray tube current as a function of slice location is determined directly for modulating tube current.

Thus, according to the disclosure patient dose is reduced and image quality is improved by modulating x-ray tube current. Image noise variation is reduced allowing more predictable image quality, and image quality is not compromised while patient dose is reduced significantly. Because no extra scout is needed, scan preparation time is significantly reduced and no extra dose is received by patient. The modulation magnitude is derived mathematically instead of empirically selected, which makes the generation of the mA modulation curves more accurate and automatic.

As such, more continuous scans can be performed without interruption because the modulated tube current heats the x-ray tube slower than the constant high tube current level. High tube current levels are also known to cause the CT data acquisition system (DAS) to over range, which results in severe shading artifacts. The disclosed subject matter can be used for any application or system which an x-ray tube current is modulated for various purposes.

Figure 5:
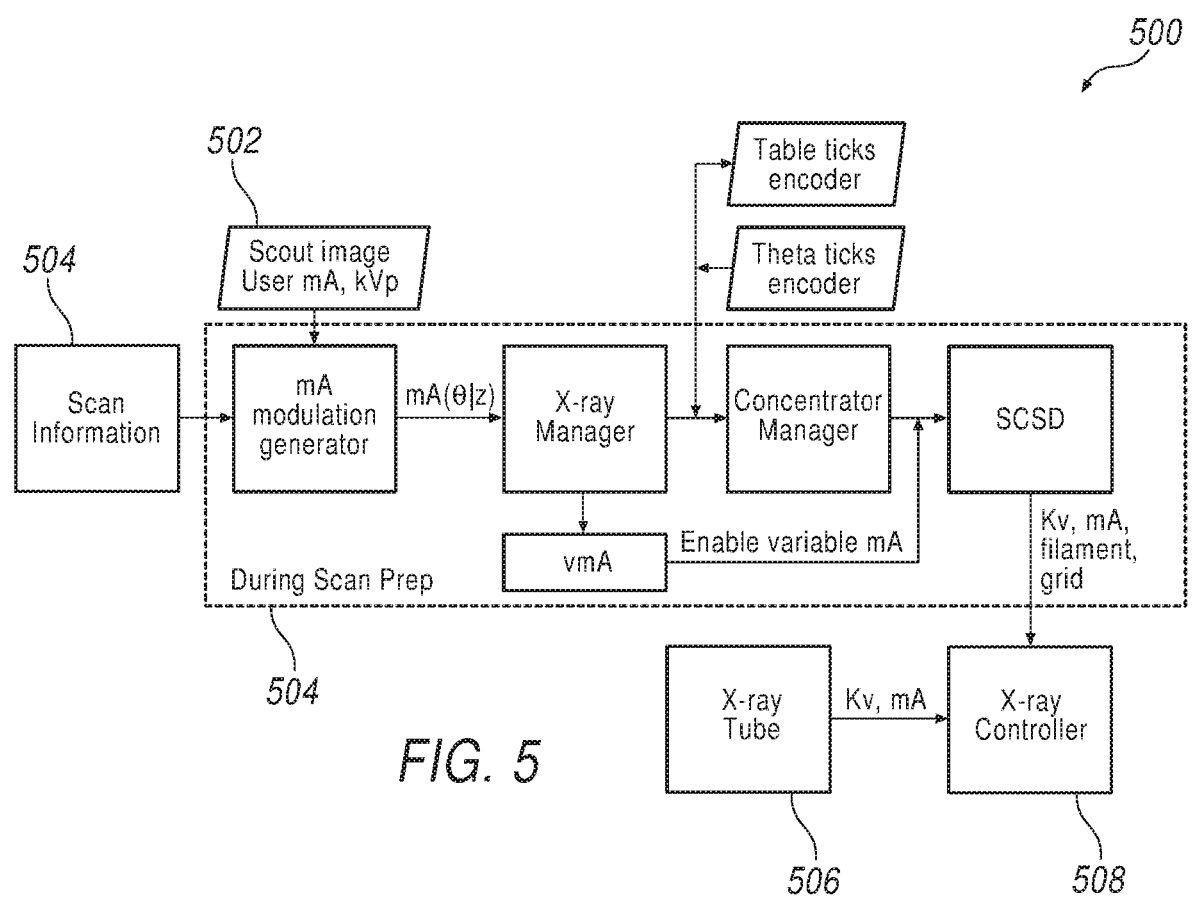
FIG. 5 illustrates a systemic work flow of the imA function, according to the disclosure.

The imA is a systematic function that includes different components working together. The components 504 include GUI, mA modulation generator, x-ray manager, concentrator/DCB firmware, SCSD board, as well as x-ray control 506 and x-ray tube 508. A corresponding systemic workflow 500 of the imA function is shown in FIG. 5. One aspect of the disclosure is the mA modulation generator, the algorithm to generate mA table for mA modulation. Performance of the algorithm is important to determining the image quality, dose reduction and x-ray tube output.

Figure 6:
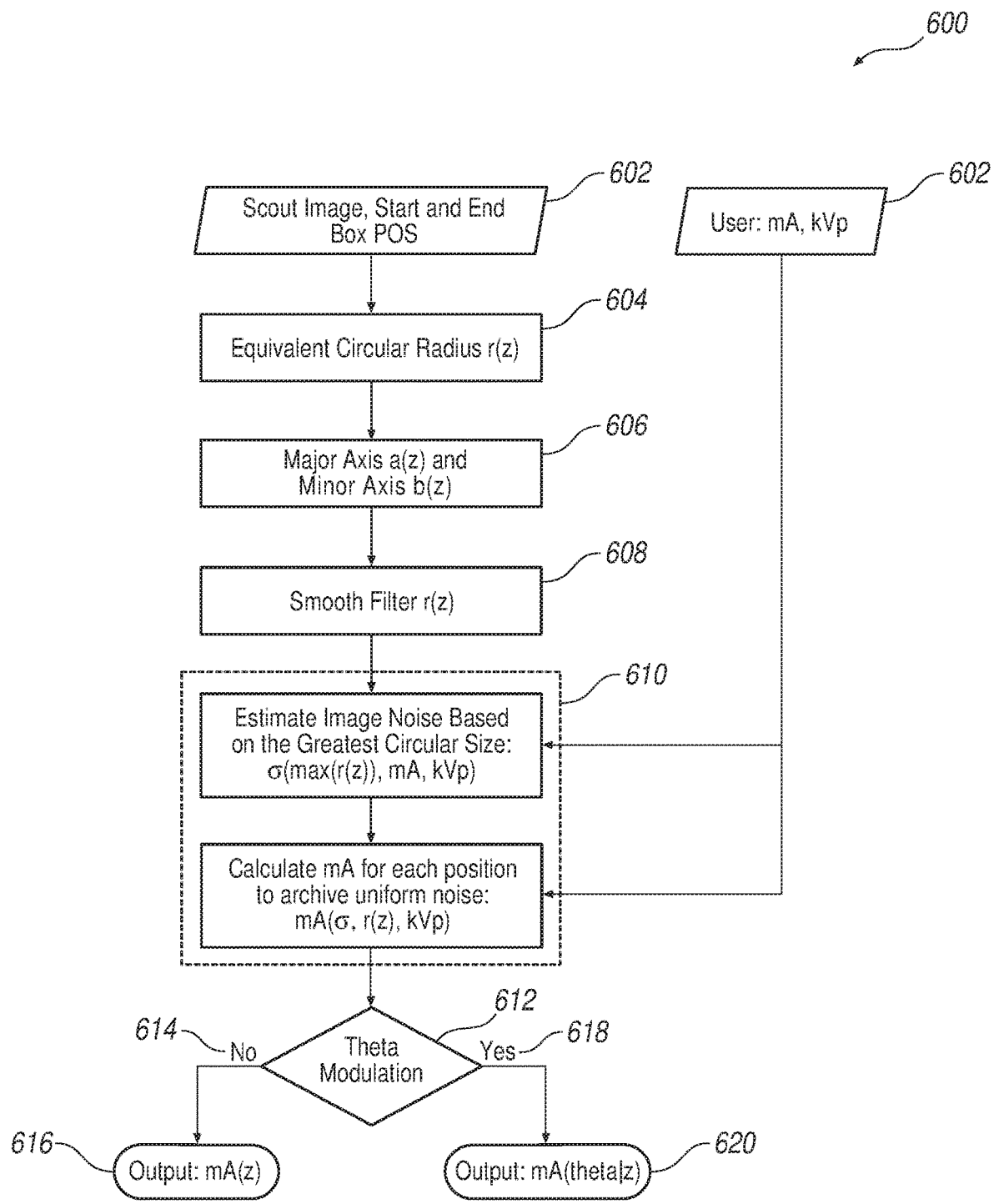
FIG. 6 illustrates an imA generator algorithm workflow, according to the disclosure.

To generate the modulated mA table, the imA modulation algorithm includes inputs such as scout image 502, scan information (mA, kV, shape filter, rotation speed, collimation, pitch for helical scan, etc.) 504 and possibly user assistance. With imA, a scout image obtained from either the anteroposterior or lateral direction is used to estimate patient-specific attenuation, and these values are then applied to calculate the modulated current for each projection to maintain image noise and decrease x-ray tube output. In this example a patient scout obtained from 0 degree, or anteroposterior, is obtained. The imA generator algorithm workflow 600 is shown in FIG. 6 and described below step-by-step.

Scout Image

A scout image I(x,z) from either the anteroposterior or lateral direction is obtained as the input of the imA generator is obtained at step 602. The patient is positioned at a center of the gantry, such as gantry 102, and the scout scan is obtained. The scout start and end table position are used to calculate the table position in z, or along the lateral direction (referring to triads 138 and 418 of FIGS. 1 and 4, respectively) for each of the modulated mA values.

Equivalent Circular Radius $r_w(z)$

At step 604, patient attenuation is measured and expressed in terms of a water cylinder having the same x-ray absorption. Specifically, a diameter of a water cylinder having the same attenuation as a cross section of the patient is determined. The water equivalent area and water equivalent diameter of such a cylinder of water are represented by $A_w$ and $D_w$, respectively. The scout image can be considered as a line integral of the scanning object. Hence, in each cross section and along the length of the object, the equivalent water area can be calculated as $$A_w(z) = \int \frac{I(x, z)}{\mu_w} dx;$$ EQN. 1, Where $\mu_w$ represents the linear attenuation coefficient of water. The equivalent diameter is calculated as:

$$D_w(z) = \sqrt{\frac{4A_w}{\pi}};$$ EQN. 2.

The equivalent water radius can be calculated as $$r_w(z) = \frac{D_w(z)}{2}.$$

Elliptical Major Axis A(z) and Minor Axis B(z)

The major axis and minor axis can be calculated 606 in several ways, according to the disclosure. One way is based on a segmentation of the scout image to estimate the dimension of the region of interest of the patient. An assumption is that attenuation of the scanned patient cross section can be equivalent to a water ellipse. Because the equivalent water radius is known, only A(z) or B(z) need to be calculated. For instance, for a 0 degree scout, the minor axis B(z) is determined as follows:

$$B(z) = \frac{\frac{1}{N}\sum_{x=-\frac{N}{2}}^{\frac{N}{2}} I(x+c,z)}{\mu_w}; \qquad \text{EQN. 3;}$$

Where c is the center pixel at each cross section, and N is the total number of pixels considered around the centerline of the scout image. The equivalent major axis can be calculated as:

$$A(z) = \frac{D_w^2(z)}{B(z)}; \qquad \text{EQN. 4.}$$

Correspondingly the major axis A(z) and B(z) can be calculated in a similar way for a lateral scout.

Smooth Filter

Figure 7:
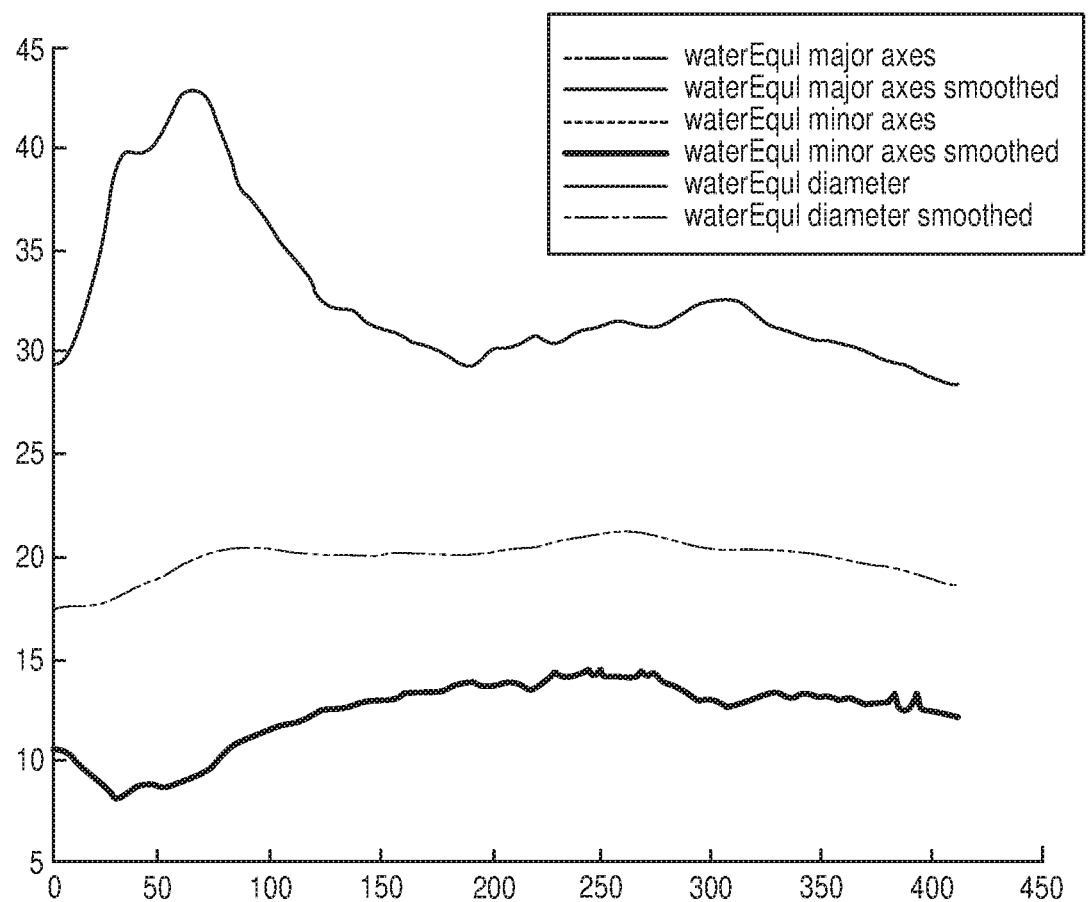
FIG. 7 illustrates calculated equivalent water diameter, major axis, minor axis and smoothed curves for an exemplary scout image.
Figure 8A:
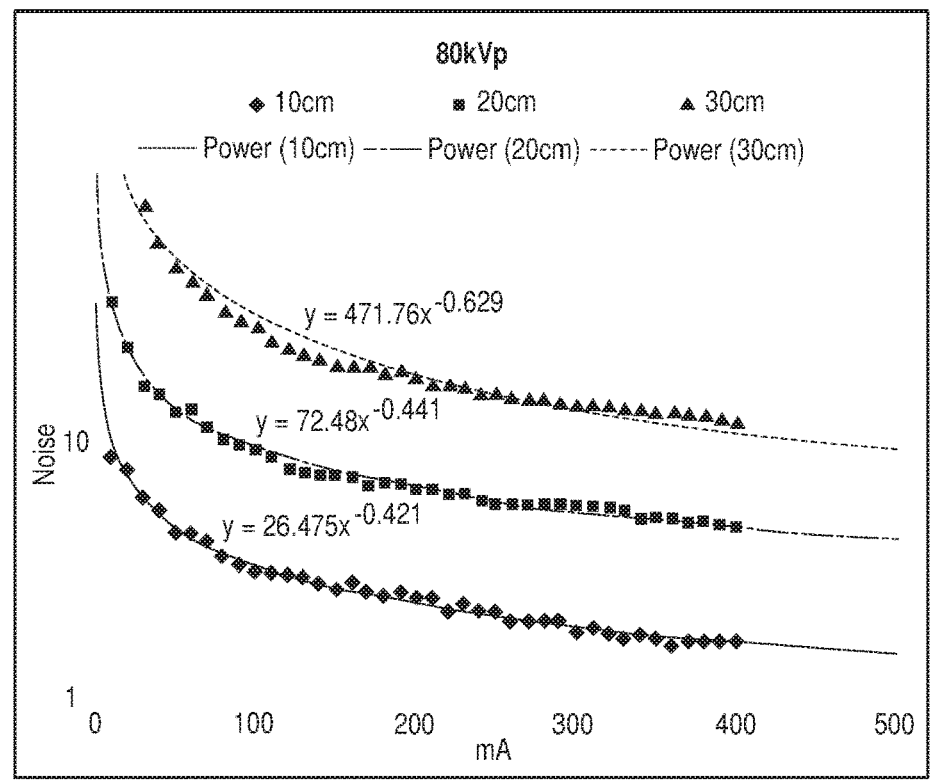
FIG. 8A illustrates exemplary relationships between mA and water phantoms for 80 kV.
Figure 8B:
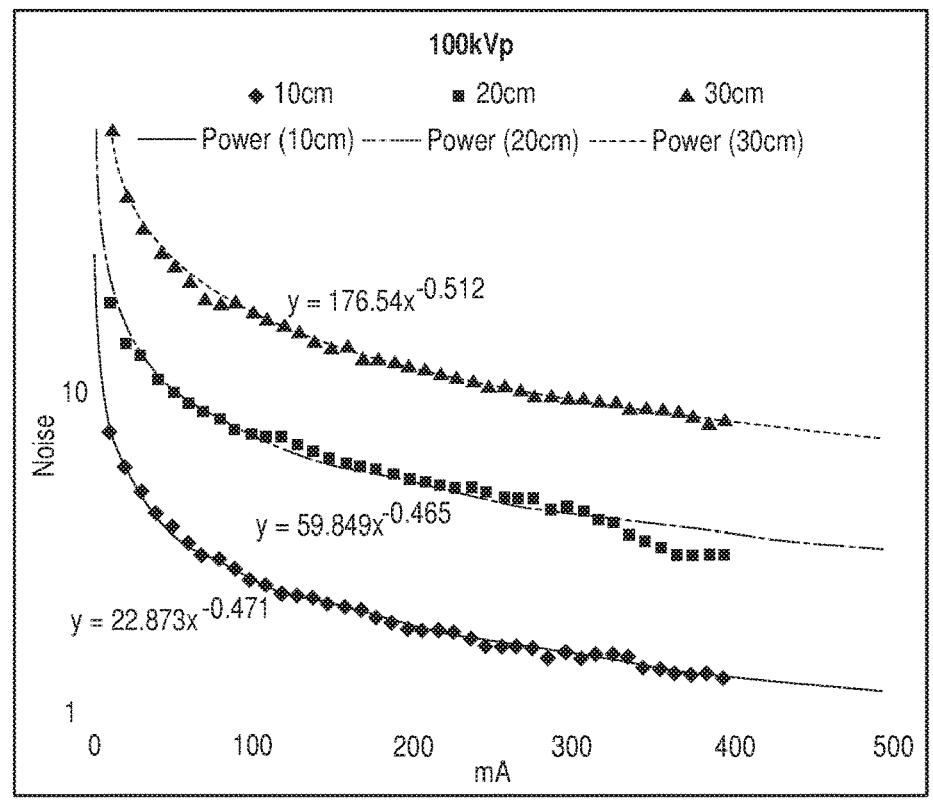
FIG. 8B illustrates exemplary relationships between mA and water phantoms for 100 kV.
Figure 8C:
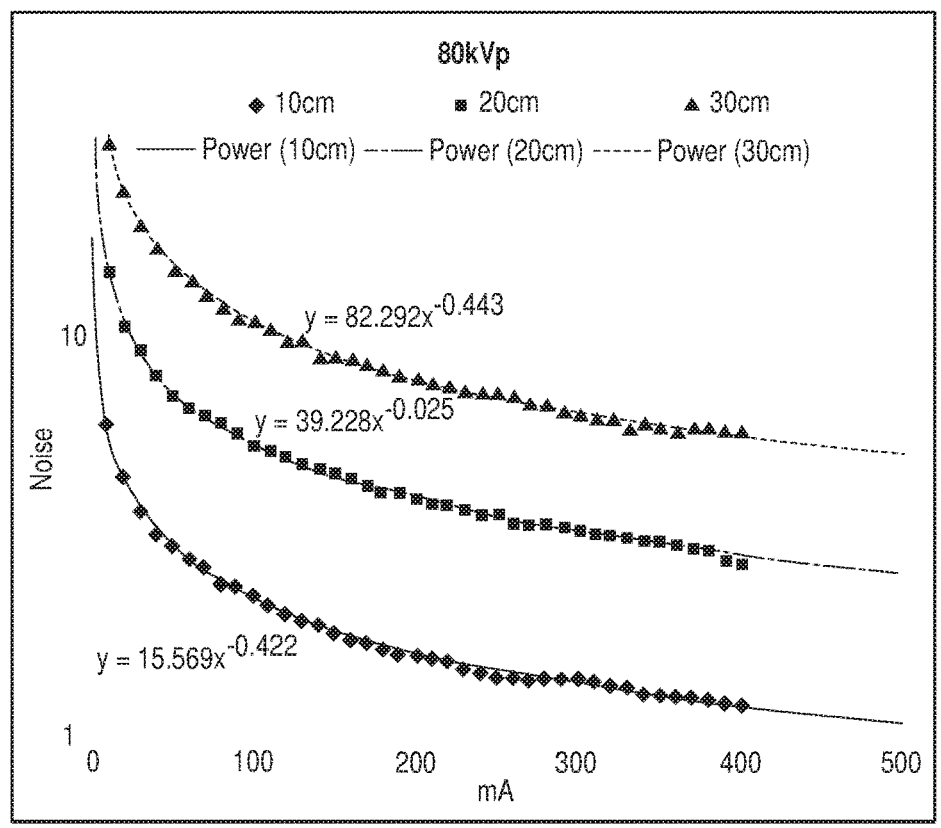
FIG. 8C illustrates exemplary relationships between mA and water phantoms for 120 kV.
Figure 8D:
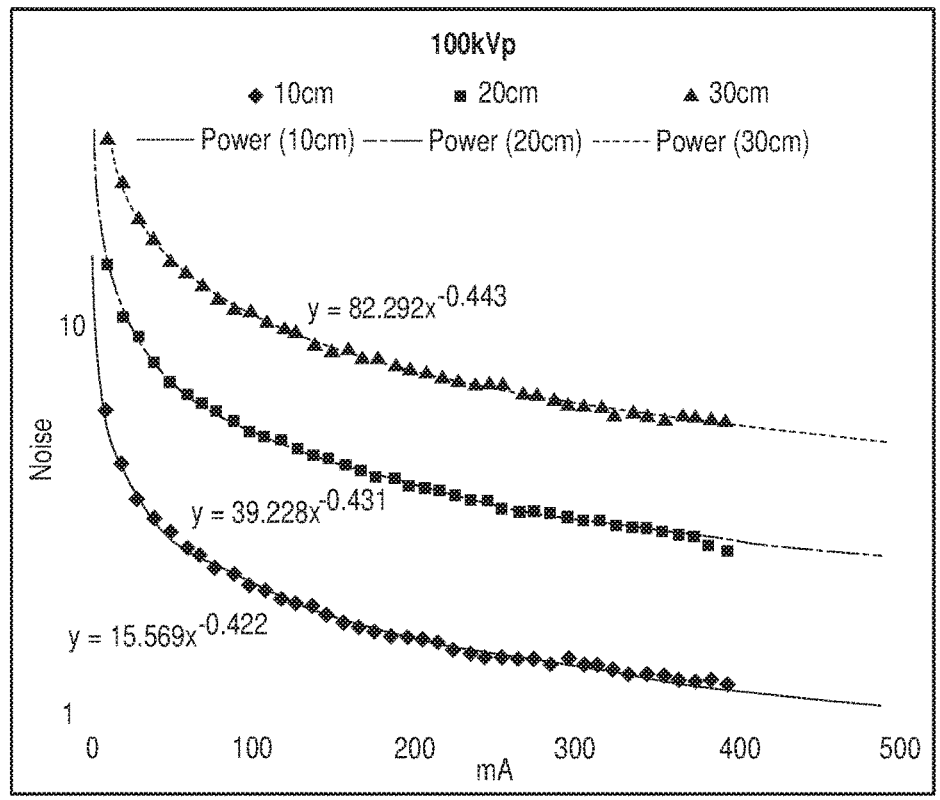
FIG. 8D illustrates exemplary relationships between mA and water phantoms for 140 kV.

Because the human body anatomical profile generally changes smoothly, a smooth filter is applied 608 to r(z), A(z), and B(z), to remove spikes. According to the disclosure, a one-dimensional box filter is applied, but other filters are contemplated. The box filter can be expressed as:

$$hf(n) = \frac{\sum_{i=\frac{L}{2}}^{\frac{L}{2}-1} f(n+1)}{L}; \qquad \text{EQN. 5;}$$

Where f(n) is the function before filtering and hf(n) is after the filtered function. Hence the filtered rf(z), Bf(z), and Af(z) are obtained. The calculated equivalent water diameter, major axis, minor axis and smoothed curves for the previously obtained scout image are shown in FIG. 7.

Noise Estimation

The purpose of the imA is to achieve equivalent image quality across different cross sections. One important image quality index is image noise. Thus, a noise relationship is built 610 between the water equivalent diameter and other scan parameters such as kVp, mA, slice thickness, reconstruction kernel, rotational speed, pitch, shape filter, etc. Given kVp, the noise relationship between mA and noise of water phantom size 10 cm, 20 cm and 30 cm are shown, as examples, in FIGS. 8A to 8D. The exemplary data was collected from a 64 slice system, helical scan, 5 mm slice thickness, STND kernel, 1s rotation, large shape filter and pitch=1. Based on the experimental or empirical results, the mA—noise relationship is expressed as:

$$\sigma = \alpha \times mA^\beta; \qquad \text{EQN. 6;}$$

given kV, water phantom size and other parameters fixed. Each kVp and phantom size has respective parameters $\alpha$ and $\beta$, and these parameters can be readily adjusted for different slice thickness, rotation speed, pitch, etc.

The noise—mA relationship for any water phantom size can therefore be derived as follows. Assuming $\sigma_1$, $\sigma_2$, are the noise for water phantom size $d_1$, $d_2$, respectively, since the noise is proportional to mA, for any water phantom size d, the noise $\sigma$ can be calculated as:

$$\sigma = \sigma_1^{t1} \sigma_2^{t2}; \qquad \text{EQN. 7;}$$

where t1 and t2 are calculated, in this example, as:

$$t1 = \frac{d_2 - d}{d_2 - d_1}; \qquad \text{EQN. 8;}$$

and $$t2 = \frac{d - d_1}{d_2 - d_1}; \qquad \text{EQN. 9}$$

In the disclosed mA algorithm, the maximum equivalent water phantom diameter $D_w^{max}$ is used to calculate the noise $\sigma_0$ as the image quality, and mA is modulated for each cross section to achieve the same noise. This noise index can also be calculated from average radius, as one example, or from a user input, as another example.

mA Modulation in z only (2D Modulation)

After calculating the noise $\sigma_0$ at the maximum water equivalent diameter $D_w^{max}$, the modulated mA values for each section can be readily calculated. Given a fixed kVp and water phantom size, the noise—mA relationship is determined:

$$mA = \frac{1}{\alpha}\sigma^{\frac{1}{\beta}}; \qquad \text{EQN. 10.}$$

Assuming the water phantom size $d_1$, $d_2$, the corresponding mA values $mA_1$, $mA_2$ to achieve the same noise level $\sigma_0$ are known. Given any water equivalent water phantom size d, the mA value to achieve the same noise level $\sigma_0$ can be calculated as:

$$mA = mA_1^{t1} mA_2^{t2}; \qquad \text{EQN. 11;}$$

with t1 and t2 defined in EQNS. 8 and 9.

According to the disclosure, additional modulation in gantry angle $\theta$ may also be determined. Thus, at step 612, if modulation in gantry angle $\theta$ is not desired 614, then mA(z) has been determined and may be applied 616 as a function of z. However, if modulation in gantry angle $\theta$ is desired 618, it may be done so 620 in the following fashion.

mA Modulation in $\theta$ (3D Modulation)

mA modulation in Z reduces noise variation allowing more predictable image quality. Dose reduction depends on the noise level aims to achieve. To further reduce the dose without significantly increasing image noise, mA modulation can be performed in x, y, z direction ($\theta$ rotational direction). The modulated mA in z for each cross section can be considered as the average mA, the mA values in $\theta$ will be further modulated based on water equivalent elliptical size. The modulated mA values in the $\theta$ direction at a given cross section can be expressed as a sinusoid curve. One example is:

$$mA(\theta|z) = mA(z) * (1 + Q(z) * \cos(2\theta + \pi)); \qquad \text{EQN. 12;}$$

where mA(z) is the modulated mA in z, and Q(z) is the modulation magnitude. Because the mA(z) can be obtained from the mA modulation in z, the only variable need to be determined is Q(z). Q(z) can be determined empirically based on the ratio of the elliptical major and minor axis. According to this example, an analytic Q(z) formula is applied to achieve the same noise level as in the mA modulation in z only. Q(z) can be calculated as $$q(Z) = \sum_{\theta=0}^{360} \frac{e^{-\mu \times \sqrt{A(z) \times B(z)}} - e^{-\mu \times l(\theta|z)}}{\cos(2\theta)e^{-\mu \times l(\theta|z)}}; \qquad \text{EQN. 13}$$

-continued where:

$$l(\theta | z) = \frac{A(z) \times B(z) \times \sqrt{1 + \tan^2\theta}}{2\sqrt{B^2 + A^2 \times \tan^2\theta}};$$ EQN. 14.

Figure 9:
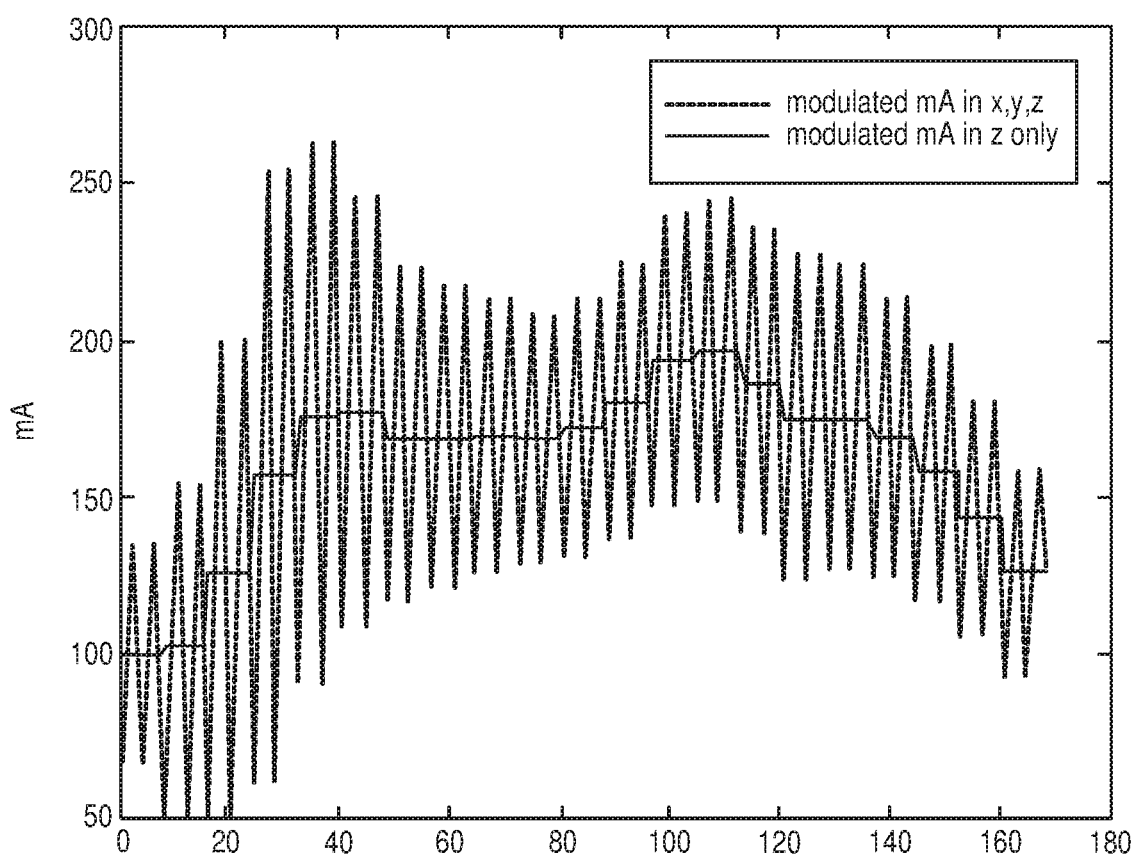
FIG. 9 illustrates an exemplary 3D modulated mA in z and theta.

The 3D modulated mA in z and theta is shown in FIG. 9. As shown, for a 0-degree scout, the mA reaches a maximum in 90 and 270 degrees direction, and reaches minimum in 0 and 180 degrees direction.

mA Modulation in Z

Figure 10A:
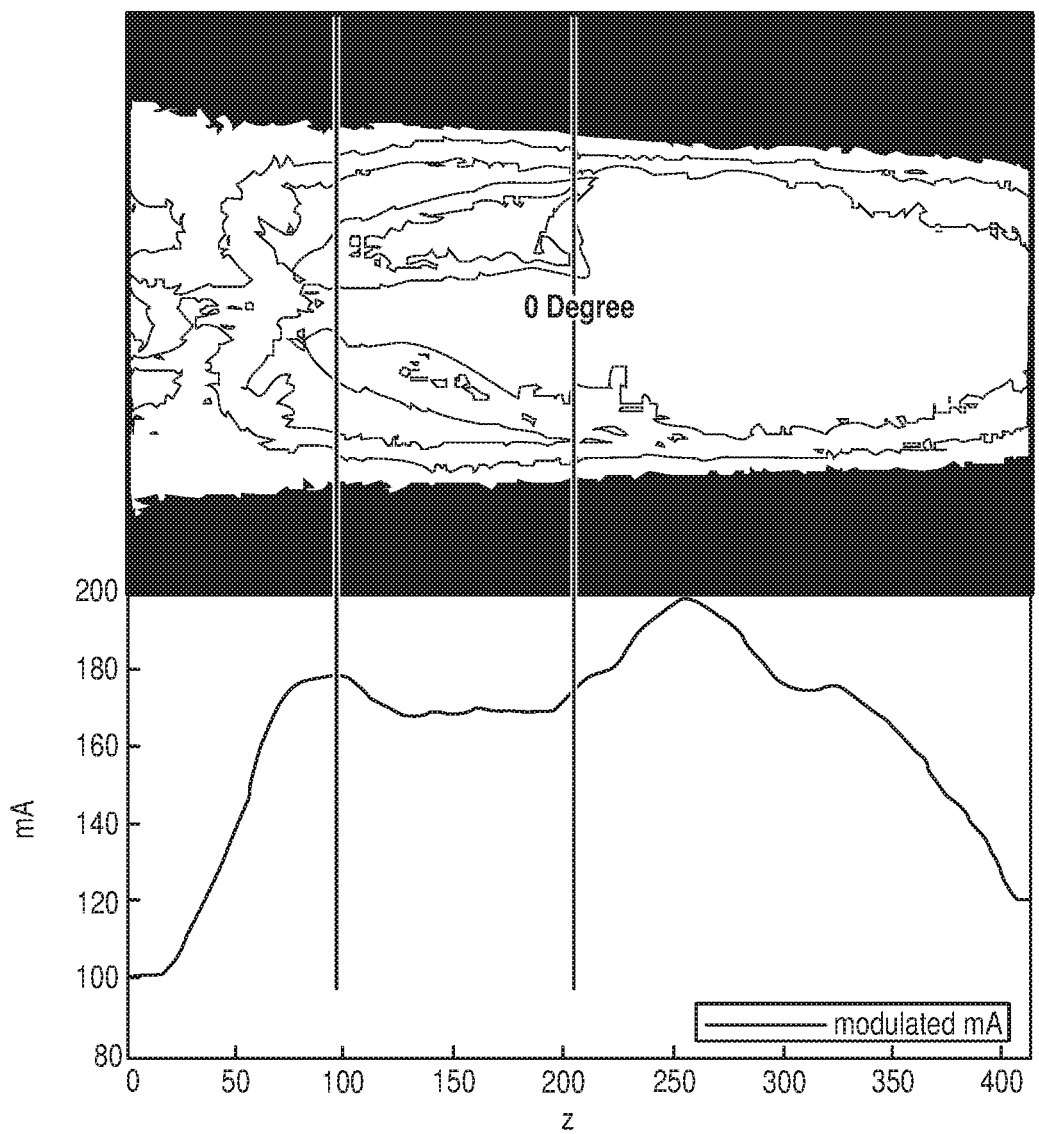
FIG. 10A shows an mA modulation in z from a 0-degree scout.
Figure 10B:
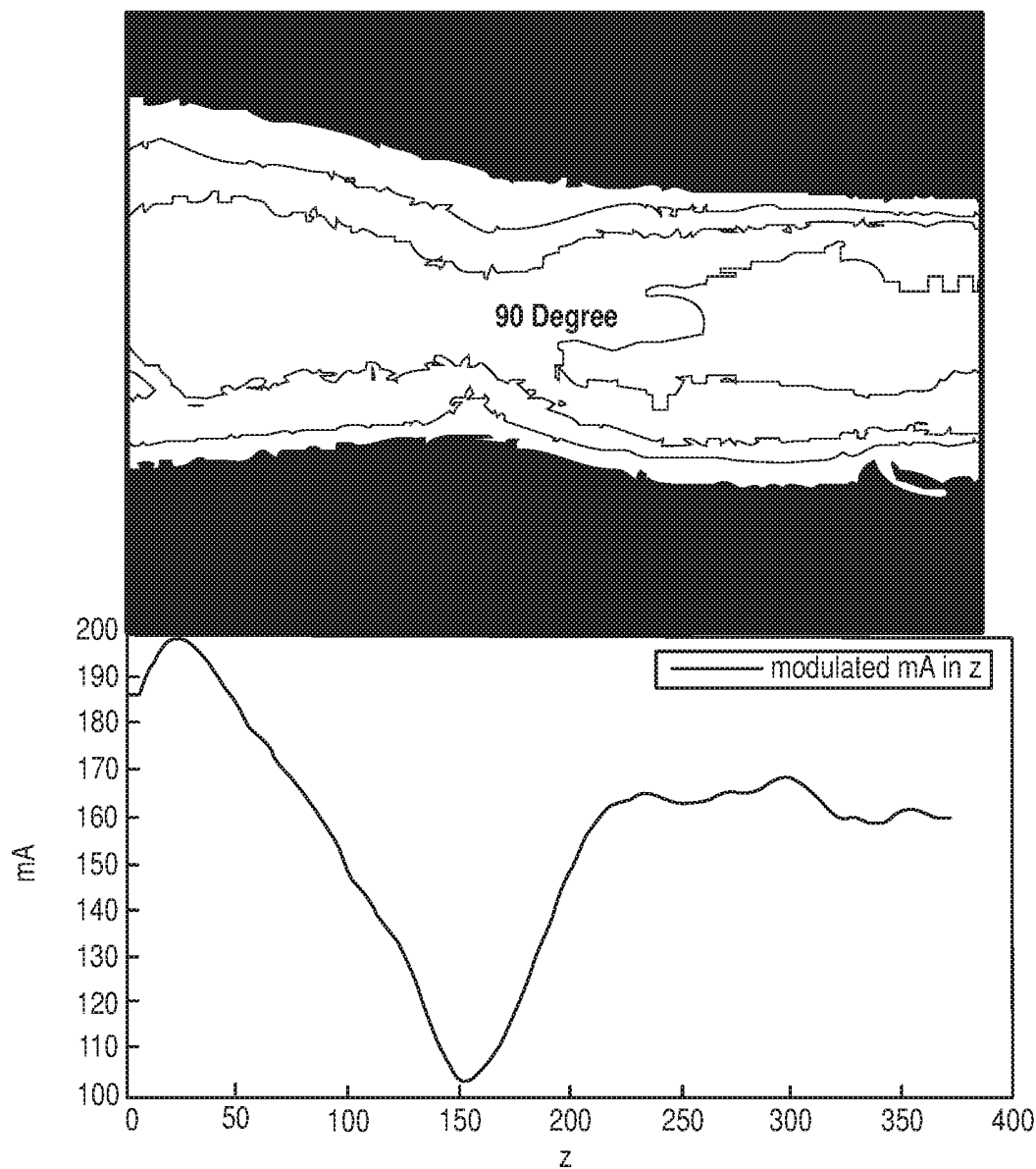
FIG. 10B shows an mA modulation in z from a 90-degree scout.

First, shown are the mA modulation in z only. FIGS. 10A and 10B show the mA modulation in z from a 0-degree scout and a 90 degrees scout, respectively. The generated modulated mA curve, as shown. matches the attenuation changes at each cross section.

mA Modulation in z and Theta

Figure 11:
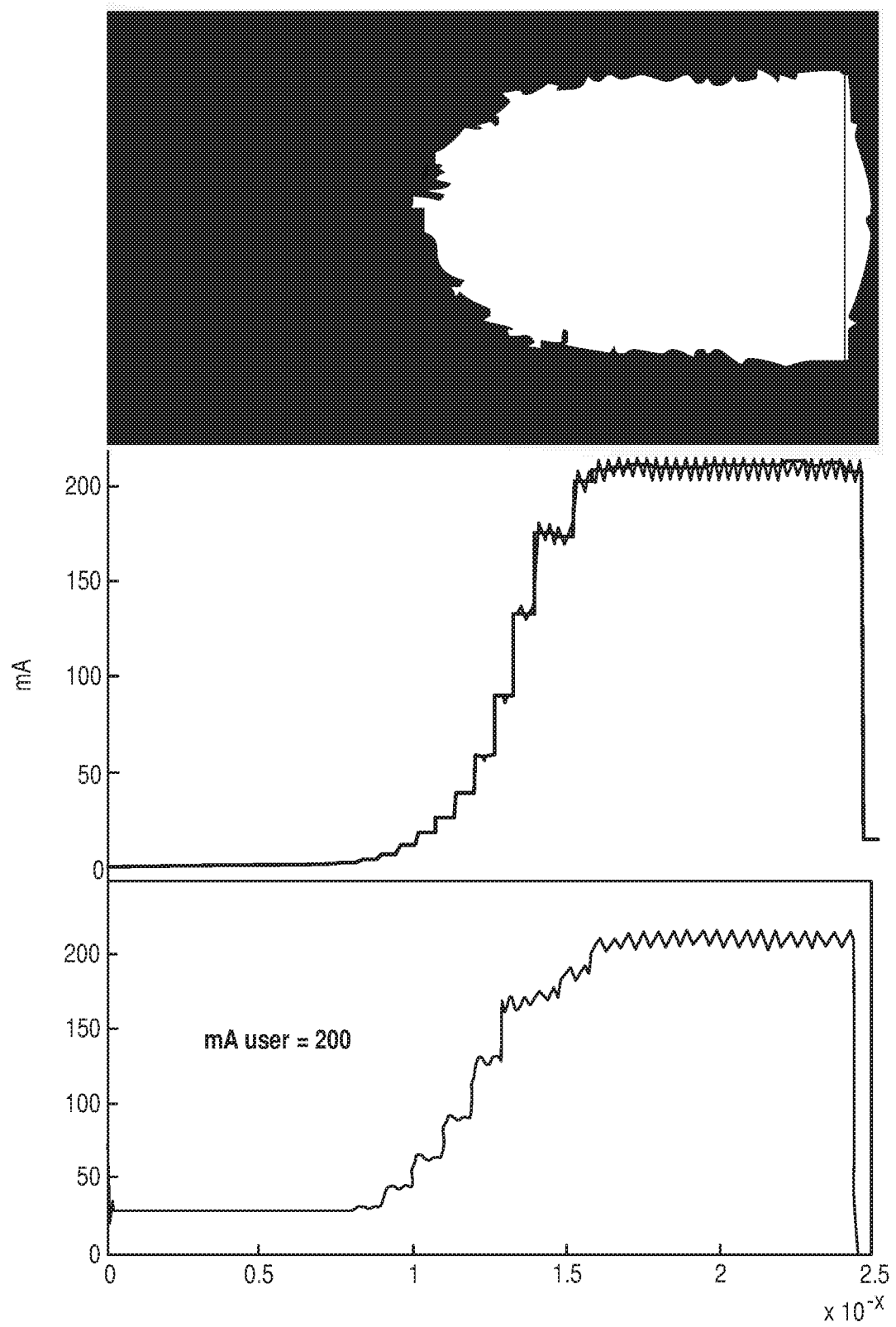
FIG. 11 illustrates an exemplary mA curve.

The imA software was integrated into a system, and a cone shape water phantom was scanned from 0 degree, using the modulated mA curve generated by the imA algorithm, and the real system mA curve. The generated mA curve, as seen in FIG. 11, matches the cone shape phantom attenuation changes at each cross section, and the real system mA curve matches the generated mA curve, as well.

When introducing elements of various embodiments of the disclosed materials, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the preceding discussion is generally provided in the context of medical imaging, it should be appreciated that the present techniques are not limited to such medical contexts. The provision of examples and explanations in such a medical context is to facilitate explanation by providing instances of implementations and applications. The disclosed approaches may also be utilized in other contexts, such as the non-destructive inspection of manufactured parts or goods (i.e., quality control or quality review applications), and/or the non-invasive inspection or imaging techniques.

While the disclosed materials have been described in detail in connection with only a limited number of embodiments, it should be readily understood that the embodiments are not limited to such disclosed embodiments. Rather, that disclosed can be modified to incorporate any number of variations, alterations, substitutions or equivalent arrangements not heretofore described, but which are commensurate with the spirit and scope of the disclosed materials. Additionally, while various embodiments have been described, it is to be understood that disclosed aspects may include only some of the described embodiments. Accordingly, that disclosed is not to be seen as limited by the foregoing description, but is only limited by the scope of the appended claims.

What is claimed is:

1. A computed tomography (CT) system, comprising:
 a rotatable gantry having an opening to receive an object to be scanned;
 a high-voltage generator;
 an x-ray tube positioned on the gantry to generate x-rays through the opening;
 a pixelated detector positioned on the gantry to receive the x-rays; and
 a computer programmed to:
  obtain a scout image of the object;
  calculate an equivalent diameter of a water cylinder based on the scout image over a length of the scout image;
  calculate a major axis and a minor axis for an equivalent ellipse over the length;
  calculate, based on a noise index and based on the equivalent diameter as the function of the length, an mA modulation as a function of the length; and
  obtain image data of the object by modulating an mA applied to the x-ray tube based on the calculated mA modulation.

2. The CT system of claim 1, wherein the computer is further programmed to:
 calculate a modulation magnitude as a function of gantry angle, based on the calculated major axis and minor axis; and
 obtain the image data by applying the modulation magnitude as the function of gantry angle.

3. The CT system of claim 1, wherein the computer is further programmed to calculate the major axis and the minor axis based on at least a total number of pixels considered around a centerline of the scout image.

4. The CT system of claim 1, wherein the computer is further programmed to apply a smooth filter of the equivalent diameter and the equivalent ellipse.

5. The CT system of claim 1, wherein the computer is further programmed to calculate the noise index based on a maximum equivalent phantom diameter of the equivalent diameter calculated over a length of the scout image.

6. The CT system of claim 1, wherein the computer is further programmed to establish a relationship between mA and noise via an empirically determination.

7. The CT system of claim 1, wherein the computer is further programmed to calculate the noise index based on the calculated equivalent diameter and based on a known relationship between mA and noise for the CT system.

8. A method of obtaining image data for a computed tomography (CT) system, comprising:
 obtaining a scout image of an object;
 calculating an equivalent diameter of a water cylinder based on the scout image over a length of the scout image;
 calculating a major axis and a minor axis for an equivalent ellipse over the length;
 calculating, based on a noise index and based on the equivalent diameter as the function of the length, an mA modulation as a function of the length; and
 obtaining image data of the object by modulating an mA applied to the x-ray tube based on the calculated mA modulation.

9. The method of claim 8, further comprising:
 calculating a modulation magnitude as a function of gantry angle, based on the calculated major axis and minor axis; and
 obtaining the image data by applying the modulation magnitude as the function of gantry angle.

10. The method of claim 8, further comprising calculating the major axis and the minor axis based on at least a total number of pixels considered around a centerline of the scout image.

11. The method claim 8, further comprising applying a smooth filter of the equivalent diameter and the equivalent ellipse.

12. The method claim 8, further comprising calculating the noise index based on a maximum equivalent phantom diameter of the equivalent diameter calculated over a length of the scout image.

13. The method of claim 8, further comprising establishing a relationship between mA and noise via an empirically determination.

14. The method of claim 8, further comprising calculating the noise index based on the calculated equivalent diameter and based on a known relationship between mA and noise for the CT system.

15. A computer readable storage medium having stored thereon a computer comprising instructions, which, when executed by a computer, cause the computer to:
   obtain a scout image of the object;
   calculate an equivalent diameter of a water cylinder based on the scout image over a length of the scout image;
   calculate a major axis and a minor axis for an equivalent ellipse over the length;
   calculate, based on a noise index and based on the equivalent diameter as the function of the length, an mA modulation as a function of the length; and
   obtain image data of the object by modulating an mA applied to the x-ray tube based on the calculated mA modulation.

16. The computer readable storage medium of claim 15, wherein the computer is further programmed to:
   calculate a modulation magnitude as a function of gantry angle, based on the calculated major axis and minor axis; and
   obtain the image data by applying the modulation magnitude as the function of gantry angle.

17. The computer readable storage medium of claim 15, wherein the computer is further programmed to:
   calculate the major axis and the minor axis based on at least a total number of pixels considered around a centerline of the scout image; and
   apply a smooth filter of the equivalent diameter and the equivalent ellipse.

18. The computer readable storage medium of claim 15, wherein the computer is further programmed to calculate the noise index based on a maximum equivalent phantom diameter of the of the equivalent diameter calculated over a length of the scout image.

19. The computer readable storage medium of claim 15, wherein the computer is further programmed to establish a relationship between mA and noise via an empirically determination.

20. The computer readable storage medium of claim 15, wherein the computer is further programmed to calculate the noise index based on the calculated equivalent diameter and based on a known relationship between mA and noise for the CT system.

\* \* \* \* \*